United States Patent [19]
Yusuf

[11] Patent Number: 6,146,646
[45] Date of Patent: Nov. 14, 2000

[54] KOKORI FRUIT-BASED COSMETIC SYSTEM

[76] Inventor: Fatimat Yusuf, 2421 Foothill Blvd. #21H, La Verne, Calif. 91750

[21] Appl. No.: 09/086,444

[22] Filed: May 28, 1998

[51] Int. Cl.[7] ..................................................... A61K 7/48

[52] U.S. Cl. ...................... 424/401; 424/195.1; 424/70.7

[58] Field of Search ................................ 424/195.1, 70.7, 424/401

[56] References Cited

U.S. PATENT DOCUMENTS 5,874,092  2/1999  Roulier et al. .......................... 424/401

Primary Examiner—Thurman K. Page
Assistant Examiner—S. Howard

[57] ABSTRACT

A method is provided for generating a cosmetic product for improving the cosmetic appearance of a person. The method comprises the steps of collecting Kokori fruit; removing an outer peel from the Kokori fruit; crushing the Kokori fruit into a pulp; and extracting Kokori liquid from the pulp of the Kokori fruit for the purpose of applying the same about eyes of a user.

5 Claims, 1 Drawing Sheet

KOKORI FRUIT-BASED COSMETIC SYSTEM

BACKGROUND OF THE INVENTION

1. Field of the Invention

The present invention relates to cosmetic devices and more particularly pertains to a new Kokori fruit-based cosmetic system for decorating eyes of a user in a new, improved manner.

2. Description of the Prior Art

The use of cosmetic devices is known in the prior art. More specifically, cosmetic devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art cosmetic devices include U.S. Pat. Nos. 4,950,478; 5,382,433; 5,215,759; 4,857,304; 4,119,712; and 4,820,510.

In these respects, the Kokori fruit-based cosmetic system according to the present invention substantially departs from the conventional concepts and designs of the prior art, and in so doing provides an apparatus primarily developed for the purpose of decorating eyes of a user in a new, improved manner.

SUMMARY OF THE INVENTION

In view of the foregoing disadvantages inherent in the known types of cosmetic devices now present in the prior art, the present invention provides a new Kokori fruit-based cosmetic system construction wherein the same can be utilized for decorating eyes of a user in a new, improved manner.

The general purpose of the present invention, which will be described subsequently in greater detail, is to provide a new Kokori fruit-based cosmetic system apparatus and method which has many of the advantages of the cosmetic devices mentioned heretofore and many novel features that result in a new Kokori fruit-based cosmetic system which is not anticipated, rendered obvious, suggested, or even implied by any of the prior art cosmetic devices, either alone or in any combination thereof.

To attain this, the present invention generally comprises a method of generating a cosmetic product with Kokori fruit for improving the cosmetic appearance of a person. Such cosmetic product exhibits improved aesthetic and practical features and a lifetime of extended duration.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Kokori fruit-based cosmetic system apparatus and method which has many of the advantages of the cosmetic devices mentioned heretofore and many novel features that result in a new Kokori fruit-based cosmetic system which is not anticipated, rendered obvious, suggested, or even implied by any of the prior art cosmetic devices, either alone or in any combination thereof.

It is another object of the present invention to provide a new Kokori fruit-based cosmetic system which may be easily and efficiently manufactured and marketed.

It is a further object of the present invention to provide a new Kokori fruit-based cosmetic system which is of a durable and reliable construction.

An even further object of the present invention is to provide a new Kokori fruit-based cosmetic system which is susceptible of a low cost of manufacture with regard to both materials and labor, and which accordingly is then susceptible of low prices of sale to the consuming public, thereby making such Kokori fruit-based cosmetic system economically available to the buying public.

Still yet another object of the present invention is to provide a new Kokori fruit-based cosmetic system which provides in the apparatuses and methods of the prior art some of the advantages thereof, while simultaneously overcoming some of the disadvantages normally associated therewith.

Still another object of the present invention is to provide a new Kokori fruit-based cosmetic system for decorating eyes of a user in a new, improved manner.

Even still another object of the present invention is to provide a new Kokori fruit-based cosmetic system that generally comprises the steps of collecting Kokori fruit; removing an outer peel from the Kokori fruit; crushing the Kokori fruit into a pulp; and extracting Kokori liquid from the pulp of the Kokori fruit for the purpose of applying the same about eyes of a user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
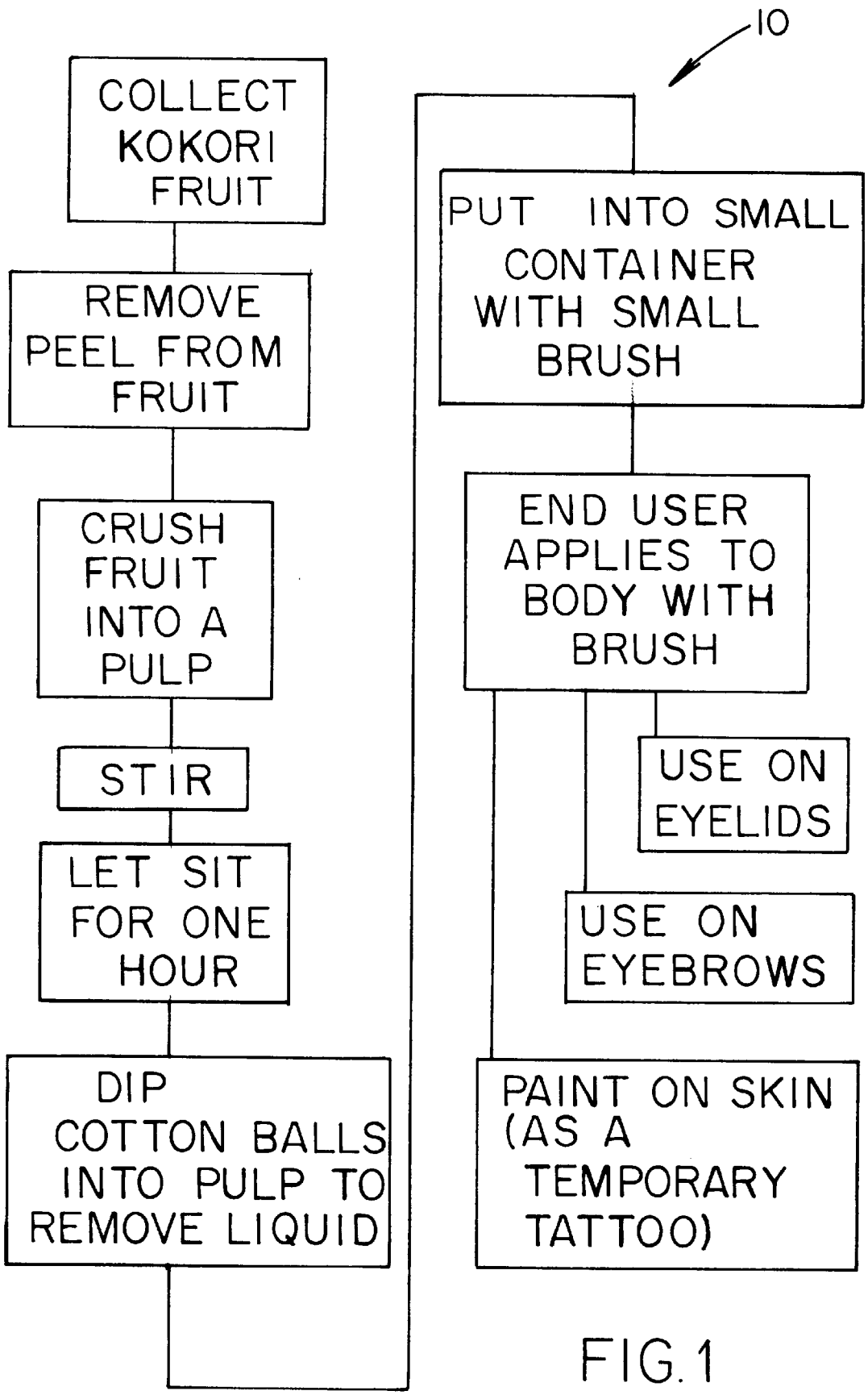
FIG. 1 is a flow diagram depicting the method of the present invention.

With reference now to the drawings, and in particular to FIG. 1 thereof, a new Kokori fruit-based cosmetic system embodying the principles and concepts of the present invention and generally designated by the reference numeral 10 will be described.

The present invention, designated as numeral 10, includes a method of generating a cosmetic product for improving the cosmetic appearance of a person. Such cosmetic product exhibits improved aesthetic and practical features and a lifetime of extended duration.

To generate the cosmetic product of the present invention, Kokori fruit is collected and an outer peel from the Kokori fruit is removed. Kokori fruit grows naturally on trees and is commonly found in Nigeria, Africa. Once the outer peel from the Kokori fruit is removed, the Kokori fruit is crushed into a pulp by way of any desired type of machine or tool.

Thereafter, the pulp of the Kokori fruit is stirred. The pulp of the Kokori fruit is then exposed to air for a period of approximately 1 hour. Such exposure is critical in that it is during this step that the pulp takes on an aesthetically pleasing dark color. After the pulp is exposed, the Kokori liquid is extracted from the pulp of the Kokori fruit with pieces of cotton.

For storage purposes, the pieces of cotton are placed within a small container having a removable brush. Such removable brush preferably is attached to a cap which is in turn screwably coupled to the container. In use, the brush is employed for applying the Kokori liquid about eyes of a user. It should be noted that the Kokori liquid may be applied to the eyebrows, eyelashes, eyelids or any other part of the body of the user as a temporary tattoo. The present invention thus enhances and brightens eyes of a user. Further, the present invention may be used to outline eyes.

By the inherent nature of the Kokori liquid, it may be easily removed if the removal is effected within one hour of its application. If, however, the Kokori liquid is left applied for at least an hour, an extended lifetime of multiple days is afforded. During such lifetime, the Kokori fruit-based cosmetic system is not subject to smudging or smearing. It has been further found that the Kokori liquid fails to stain clothing.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method of generating a cosmetic product for improving the cosmetic appearance of a person which has an extended duration, the method comprising the steps of:

collecting Kokori fruit;

removing an outer peel from the Kokori fruit;

crushing the Kokori fruit into a pulp;

stirring the pulp of the Kokori fruit;

exposing the pulp of the Kokori fruit to air for a period of approximately 1 hour;

soaking Kokori liquid from the pulp of the Kokori fruit with pieces of cotton;

placing the pieces of cotton within a small container having a removable brush; and applying the Kokori liquid about eyes of a user with the brush.

2. A method of generating a cosmetic product for improving the cosmetic appearance of a person, the method comprising the steps of:

collecting Kokori fruit;

removing an outer peel from the Kokori fruit;

crushing the Kokori fruit into a pulp; and extracting Kokori liquid from the pulp of the Kokori fruit for the purpose of applying the same on skin of a user.

3. A method as set forth in claim 2 wherein the liquid is extracted with pieces of cotton.

4. A method as set forth in claim 2 wherein the Kokori fruit is exposed to air prior to the application of the Kokori liquid on the user.

5. A method as set forth in claim 4 wherein the exposure lasts for approximately one hour.

* * * * *